United States Patent [19]

Kemp et al.

[11] Patent Number: 5,772,985
[45] Date of Patent: *Jun. 30, 1998

[54] METHOD FOR TREATING BOVINE HAIRY HEEL WARTS

[75] Inventors: G. Kere Kemp, Mercer Island, Wash.; Robert D. Kross, Bellmore, N.Y.

[73] Assignee: Alcide Corporation, Redmond, Wash.

[ * ] Notice: The term of this patent shall not extend beyond the expiration date of Pat. No. 5,384,134.

[21] Appl. No.: 525,903

[22] Filed: Sep. 8, 1995

[51] Int. Cl.[6] .............................. A61K 9/12; A61K 33/14
[52] U.S. Cl. ......................... 424/45; 424/78.02; 424/661; 424/630; 424/665
[58] Field of Search .................................. 424/45, 78.02, 424/661, 630, 665; 514/886, 887

[56] References Cited

U.S. PATENT DOCUMENTS

| | | | |
|---|---|---|---|
| Re. 31,779 | 12/1984 | Alliger | 252/187.23 |
| 4,330,531 | 5/1982 | Alliger | 424/149 |
| 4,891,216 | 1/1990 | Kross et al. | 424/78 |
| 4,956,184 | 9/1990 | Kross | 424/661 |
| 4,986,990 | 1/1991 | Davidson et al. | 424/665 |
| 5,100,652 | 3/1992 | Kross et al. | 424/53 |
| 5,185,161 | 2/1993 | Davidson et al. | 424/665 |
| 5,384,134 | 1/1995 | Kross et al. | 424/661 |
| 5,389,390 | 2/1995 | Kross | 426/332 |

FOREIGN PATENT DOCUMENTS

| | | |
|---|---|---|
| 0287974A2 | 10/1988 | European Pat. Off. . |
| 85/04107 | 9/1985 | WIPO . |
| 89/10747 | 11/1989 | WIPO . |

*Primary Examiner*—Raj Bawa
*Attorney, Agent, or Firm*—Seed and Berry LLP

[57] ABSTRACT

Compositions and methods for the treatment of mammalian skin lesions are provided. The compositions contain a protic acid and a chlorite ion, and may be applied topically to a lesion to promote healing. The compositions and methods are particularly useful in the dairy industry for the treatment of bovine hairy heel warts.

12 Claims, 1 Drawing Sheet

METHOD FOR TREATING BOVINE HAIRY HEEL WARTS

TECHNICAL FIELD

The present invention relates generally to the treatment of mammalian skin lesions and, more specifically, to compositions and methods useful for treating bovine hairy heel warts.

BACKGROUND OF THE INVENTION

Skin lesions are a source of discomfort and a potential health hazard for animals, including humans. Hairy heel warts, also known as digital dermatitis or papillomatous digital dermatitis, represent a form of skin lesion that is epidemic in many dairy herds throughout the United States. This disease, which was first reported in Italy in 1974 and in New York in the late 1970s, has affected cattle in forty or more states in the United States, and many other countries have reported animals with similar lesions.

Bovine hairy heel warts begin as small eroded or ulcerative areas between the bulbs of the heel. As the lesion progresses, granulation tissue forms which, with outgrowths of dermal tissue and keratin, grossly looks like hair. Even though the lesion is termed a "wart," there is no diagnostic evidence to support viral involvement.

As a result of the lesions between the bulbs of the heel, affected animals tend to avoid use of the limb where the lesion is located, or to shift weight from the heel to the toe. The painful lameness related to these lesions can cause the cow's feed intake to drop due to her reluctance to move to the feed bunk or stand to eat. Lameness can also cause a reluctance to show signs of estrus. As a result of decreased feed intake, a single cow's milk production may decrease by more than sixteen pounds per day. In some herds, more than 15% of the cows may be affected by hairy heel warts, which results in a significant loss of daily milk production. Such losses may range between about $22 and $30 per day for each 100 lactating cows. Additional income may be lost due to treatment costs and milk discarded to avoid residues.

Hairy heel warts have been treated in a number of ways. Surgical excision is the most labor-intensive and expensive approach. Successful treatment by use of parenteral antibiotics has been reported, but has not been found to be reproducible. Application of oxytetracycline under a bandage is effective, but bandaging affected hooves may be labor-intensive in large or heavily afflicted herds. The most common treatment method employs foot baths containing dilute solutions of formaldehyde or copper sulfate, but such methods have proved only partially effective. In addition, formaldehyde foot baths are expensive and may pose human health hazards. The use of dilute tetracycline or lincocin-spectinomycin foot baths has also been reported. However, foot baths can be difficult to manage in large herds, due to the necessity for solution changes.

Topical spray application may offer a more efficient and selective approach to treatment of bovine hairy heel warts. However, an effective spray treatment is not presently available. Accordingly, there is a need in the art for improved compositions and methods for treatment of skin lesions such as bovine hairy heel warts, including compositions effective by spray application. The present invention fulfills these needs and provides for the related advantages.

SUMMARY OF THE INVENTION

In brief, this invention is directed to compositions and methods useful for treating mammalian skin lesions, including bovine hairy heel warts. In one aspect, the present invention provides methods for treating a mammalian skin lesion, comprising topically applying to a lesion an effective amount of an aqueous composition comprising a protic acid and a chlorite ion. Optionally, the composition may further comprise a wetting agent, a film forming agent, an alcohol, a wound-healing agent, a preservative and/or a colorant. In a preferred embodiment, the method further comprises the step of mixing a first phase and a second phase prior to applying the composition to the lesion, wherein the first phase comprises the protic acid and the second phase comprises the chlorite ion.

In a related aspect, this invention provides methods for treating a bovine hairy heel wart, comprising applying to a bovine hairy heel wart an effective amount of the above aqueous composition.

These and other aspects of the present invention will become apparent upon reference to the following detailed description and attached drawing.

DETAILED DESCRIPTION OF THE INVENTION

Figure 1:
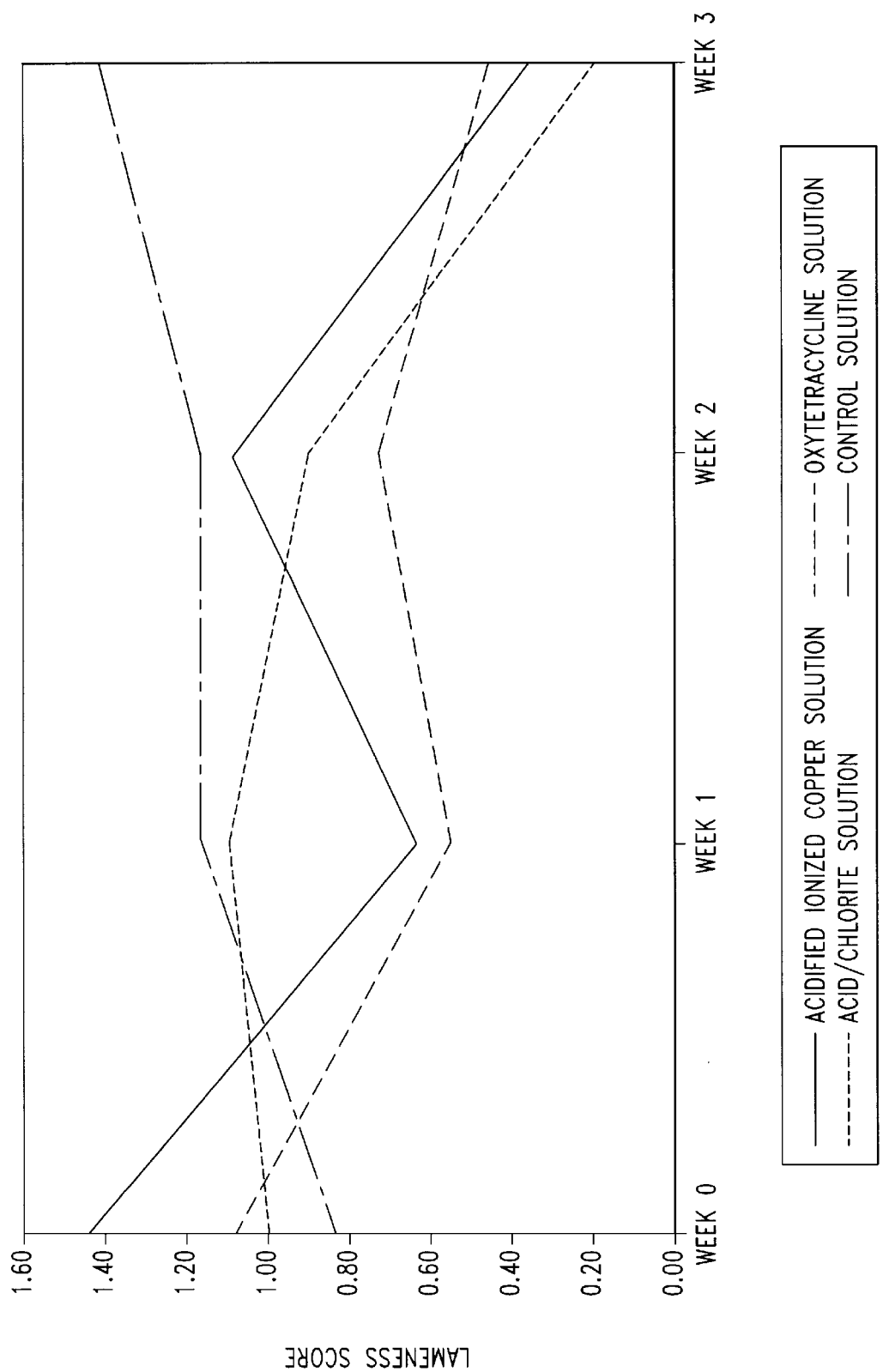
FIG. 1 shows the change in lameness score observed over a three week period of treatment with a representative composition according to this invention, as compared to treatment with an oxytetracycline solution, a copper-containing solution and a placebo solution.

As noted above, the present invention is generally directed to compositions and methods for the treatment of mammalian skin lesions, such as bovine hairy heel warts. The compositions of this invention are aqueous solutions comprising a protic acid and a chlorite ion. Optionally, the compositions may further comprise additional components such as a wetting agent to facilitate skin penetration, a film-forming agent and/or a wound-healing agent, such as copper. The compositions of this invention may be applied topically (e.g., by spray application) to a skin lesion to facilitate healing.

In the context of the present invention, the term "protic acid" refers to any acid or mixture of acids (including organic acids and inorganic acids) capable of providing an ionizable hydrogen (i.e., a proton) and reducing the pH of the composition to below about 6. Representative organic acids include, but are not limited to, α-hydroxy acids of the general formula:

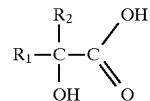

wherein $R_1$ and $R_2$ are independently selected from hydrogen, methyl, $-CH_2COOH$, $-CH_2OH$, $-CHOHCOOH$ and $-C_6H_5$. In a preferred embodiment, the protic acid is an organic acid having a pK ranging from about 2.8 to about 4.2, and more preferably from about 3.0 to about 4.0. Typical organic acids include citric, malic, tartaric, glycolic, mandelic and/or lactic acid. More preferably, the protic acid is mandelic acid. Inorganic acids include, but are not limited to, acids having a pK ranging from about 0 to about 2.2, such as sulfuric, hydrochloric, nitric and/or phosphoric acid.

Those of ordinary skill in the art will recognize that the concentration of protic acid in the composition will vary depending upon the strength of the protic acid. Organic acids will generally be present in an amount ranging from about 0.05% to about 5%, preferably from about 0.1 % to about 2%, by weight of the composition. Stronger inorganic acids will generally be present in an amount ranging from about 0.005% to about 0.5% by weight of the composition. In either case, the amount of protic acid in the composition is sufficient to lower the pH of the composition to below about 6, preferably from about 2 about 5, and more preferably from about 2.5 to about 4.

The chlorite ion component is preferably produced by aqueous disassociation of a water soluble chlorite, such as a metal chlorite. The term "metal chlorite" encompasses both alkali metal chlorites and alkaline earth metal chlorites, including the so-called "stabilized chlorine dioxide" products that contain a metal chlorite. Sodium chlorite and potassium chlorite are preferred, with sodium chlorite being particularly preferred.

The chlorite ion is typically present in the composition in an amount ranging from about 0.01 % to about 1.0% by weight. Preferably, the chlorite is present in an amount ranging from about 0.05% to about 0.75%, and more preferably from about 0.1% to about 0.65%, by weight of the composition.

In the practice of this invention, the protic acid and chlorite ion react to generate chlorous acid. The chlorous acid then degrades, via a series of cidal intermediates, partially converting to cidal chlorine dioxide, which ultimately dissipates. Without intending to be limited by any particular theory, it is believed that the chlorous acid and the resulting oxidative compounds are the source of the therapeutic effect of the present compositions.

Since the level of oxidative compounds within the acid/chlorite composition decreases with time, the composition is preferably formulated to allow combination of the protic acid and chlorite ion immediately prior to use (i.e., preferably within 4 hours, and more preferably within 1 hour, of application). Thus, while the composition may be provided in a single aqueous solution, the composition is more preferably provided in two phases, with one phase containing the protic acid and the other containing the chlorite ion. The two phases may then be combined prior to application in suitable ratios to achieve the above concentrations. Preferably, the two phases are formulated such that they are combined in approximately equal parts by volume.

Optionally, the composition additionally comprises one or more of the following: a wetting agent, a film forming agent, an alcohol, a wound-healing agent, a preservative, and/or a colorant. In a composition provided in two phases, the optional components are preferably provided within the protic acid-containing phase.

A wetting agent is any compound added to the composition to facilitate penetration of the skin lesion. Suitable wetting agents include (but are not limited to) non-ionic surfactants, such as alkylphenoxy polyoxyethylenes or poly(oxyethylene/oxypropylene) copolymers; anionic surfactants, such as alkylaryl sulfonates; and cationic surfactants, such as cetylpyridinium chloride The amount of wetting agent in the composition will depend upon the nature and size of the wetting agent molecule, but generally ranges from about 0.005% to about 0.5%, typically from about 0.05% to about 0.3 % by weight of the composition.

The optional wound-healing agent may be any compound known to facilitate the healing of wounds. Preferably, the wound-healing agent is a copper containing compound, such as copper sulfate, which provides ionic copper (II) in an acid environment. More preferably, the composition contains copper in an amount ranging from about 100 ppm to about 4000 ppm, and more preferably about 2500 ppm.

One or more film forming agents may also be included within the composition. A film forming agent is a component that increases the membranous or film-like character of the composition after application to a skin lesion and evaporation of the solvent. Any appropriate water-soluble polymer or polymers may be employed, such as polyacrylamide (or derivatives thereof) and poly(alkylene oxide) polymers or block copolymers. The amount of film forming agent depends upon the size and properties of the polymer(s), but generally ranges from about 0.1% to about 1.0%, typically from about 0.25% to about 0.75%, by weight of the composition.

The optional alcohol component may comprise any alcohol or alcohols known to those of ordinary skill in the art to hasten evaporation of the solvent phase, as well as facilitate dissolution of the film forming agent(s). Suitable alcohols include ethyl, propyl and/or isopropyl alcohol. In general, the amount of alcohol ranges from about 2% to about 25%, and typically from about 5% to about 15% by weight of the composition.

As mentioned above, the optional preservative is present in the protic acid-containing phase, and comprises any suitable preservative known in the art to be stable and functional in an acid environment, including (but not limited to) benzyl alcohol and sodium benzoate. Such preservatives may comprise up to about 0.1%, typically from about 0.02% to about 0.05%, and preferably from about 0.02% to about 0.04% by weight of the protic acid-containing phase.

The optional colorant may be any suitable dye known in the art to be stable in the acid and/or chlorite phases, including (but not limited to) FD&C Yellow No. 5 and methylene blue.

The compositions of this invention may be applied topically to a skin lesion, by any appropriate means known to those of ordinary skill in the art. For example, the compositions may be painted onto the affected area or may be applied using a footbath. Preferably, the compositions are applied by spraying, using a spray bottle or pump. In the practice of this invention, the use of a relatively wide aperture may be beneficial for spraying. The composition is typically applied to the lesion one or more times per day until the lesion is adequately healed. The amount of the composition applied to a lesion, such as a hairy heel wart, generally ranges from about ⅛ oz. to about 1 oz., and preferably from about ¼ oz. to about ½ oz. Bandaging of the affected area following application is not essential, but may result in more rapid healing.

The present invention is illustrated by the following examples, which are to be regarded as illustrative rather than restrictive. Unless otherwise noted, all parts and percentages in the examples, as well as the specification and claims, are by weight.

EXAMPLES

Preparation of a Composition for Treating Hairy Heel Warts

Example 1

This example illustrates the preparation of a representative composition for treating bovine hairy heel warts.

A protic acid phase was prepared by mixing the following ingredients:

| Component | Composition |
| --- | --- |
| Mandelic Acid | 5.00% |
| Sulfuric Acid (1N) | 2.00% |
| Cyanamer N300LMW | 0.75% |
| Poloxamer 188 | 0.62% |
| Sodium Benzoate | 0.04% |
| Isopropanol | 15.00% |
| Deionized Water | q.s. |

A chlorite ion phase was prepared by mixing the following ingredients:

| Component | Composition |
| --- | --- |
| Sodium Chlorite | 1.00% |
| Cyanamer N300LMW | 0.75% |
| Sodium Hydroxide | 0.032% |
| Triton X-100 | 0.045% |
| EDTA, $Na_4$ | 0.19% |
| Isopropanol | 15.00% |
| Polyethyleneglycol 4600 | 0.30% |
| Methylene Blue | 0.01% |
| Deionized Water | q.s. |

The two phases were blended in approximately equal volumes, to form a solution of pH 3.0, just prior to application. The film-forming agents within the composition suppress the penetration of external bacteria while the causative bacteria are being destroyed by the chlorous and mandelic acid germicidal agents.

Example 2
Preparation of an Alternate Composition for Treating Bovine Hairy Heel Warts This example illustrates the use of an inorganic protic acid within a composition for treating bovine hairy heel warts, in which the two phases are provided as concentrates.

A protic acid concentrate phase is prepared by mixing the following ingredients:

| Component | Composition |
| --- | --- |
| Phosphoric Acid (85% tech.) | 0.94% |
| Sodium Dodecylbenzenesulfonate | 0.26% |
| Deionized Water | q.s. |

A chlorite ion concentrate phase is prepared by mixing the following ingredients:

| Component | Composition |
| --- | --- |
| Sodium Chlorite | 16.72% |
| Deionized Water | q.s. |

Prior to use, the two phases are added to water, in a volume ratio of 1 part of each phase to 24 parts of water, with stirring after the serial addition of each phase. The pH of the mixture is 2.5–2.6.

Example 3
Preparation of a Bi-active Composition for Treating Bovine Hairy Heel Warts This example illustrates the preparation of a composition for treating bovine hairy heel warts, where the composition includes an ionized copper acid salt.

A protic acid phase is prepared by mixing the following ingredients:

| Component | Composition |
| --- | --- |
| Lactic Acid | 2.64% |
| Triton X-100 | 0.10% |
| Copper Sulfate, pentahydrate | 0.50% |
| Sulfuric Acid (1N) | q.s. - >pH 3.0 |
| Deionized Water | q.s. |

A chlorite ion phase is prepared by mixing the following ingredients:

| Component | Composition |
| --- | --- |
| Sodium Chlorite | 0.64% |
| Sodium Benzoate | 0.40% |
| Sodium Hydroxide (1N) | q.s. - >pH 11.0 for mixture |
| Deionized Water | q.s. |

The two phases are blended in approximately equal volumes, to form a solution of pH 3.0, just prior to application. In this formulation, the antimicrobial effects of the chlorous acid are supplemented by that of residual lactic acid as well as that of benzoic acid which is formed upon combination of the phases. Adding to that action are the beneficial effects provided by the acidified copper salt.

Example 4
Treatment of Bovine Hairy Heel Warts

This example illustrates the use of the representative acid/chlorite composition of Example 1 for the treatment of bovine hairy heel warts. The effectiveness of this composition was compared to that of two other treatment compositions (a 100 mg/cc oxytetracycline solution and an acidified ionized copper solution (HOOFPRO, SSI Corp., Los Gatos, Calif.)), as well as an aqueous placebo.

The trial was conducted on a 1,060-cow commercial Holstein dairy herd in Wisconsin. The herd was housed in two identical free stall barns with four groups of 104 cows in each barn. Cows were milked three times daily in two identical double-8 herringbone milking parlors. The herd was a closed herd, and each group contained equal proportions of both primiparas and multiparas lactating animals. Milking cows in all groups were uniformly mixed in age, days in milk, milk production, and general health conditions. All groups were fed the same TMR mix.

Cows showing any type of heel wart lesions were selected from four of the eight milling groups on the farm. The cows were moved to a chute where the rear feet of all cows were examined. Cows with foot lesions other than heel warts which could cause lameness were omitted from the trial. Upon selection for the trial, each cow was scored using a lameness scale, as discussed below. Cows were then randomly assigned to one of four trial groups and marked with colored tape on their tails and both rear legs just above the dew claws for identification purposes. Cows were divided so that equal numbers of trial cows were placed in four of the eight milking groups and two of the trial groups were milked through each parlor.

The trial solutions were stored in one gallon jugs and poured into 500 ml color-coded spray bottles for application. The herd veterinarian, who was on the farm daily, supervised the filling of the bottles and the use of the solutions by the employees who milked the cows. Milkers, using color codes and computer lists to identify the trial cows, washed the affected area of the heel with a water hose prior to spraying the affected area with the appropriate solution.

During the trial period of three weeks, each cow was treated with sufficient liquid to cover the affected hoof as it came through the parlor at each of the three daily milkings. The trial group treated with the composition of Example 1 missed two days of treatment during the middle of the trial. To equalize the trial days with the other three groups, this group received treatment for two days longer than the other groups at the end of the trial period.

The lameness score given to each cow at the initial evaluation was as follows: 0—no visible lameness; 1—slight lameness at some gaits; 2—noticeable lameness while walking; and 3—severe lameness, limited weight bearing while standing or walking. During the next three weeks, cows were scored weekly for lameness using the same scoring method. Degree of lameness was evaluated by watching trial cows walk on concrete in the free-stall feeding area. To isolate individual trial cows during the lameness evaluation, the entire pen of cows was grouped in one section and the trial cows were observed individually as they walked at a normal pace in the vacant concrete alley.

The results of the lameness scoring were analyzed using the personal computer version of Statistical Analysis System. Two cows in the control group were removed from the herd due to excessive lameness before the end of the trial, and their final lameness scores were recorded as "3" (severe lameness). In order to minimize variations in individual cow conditions at the start of the trial, the change in lameness score over the three-week trial was calculated for each trial animal by subtracting the initial lameness score from the final score.

Due to the non-parametric nature of this scoring system, the change in score for each animal was first ranked and then the mean ranking for each trial group was compared using the General Linear Model (GLM) procedure. Least Significant Difference (LSD) pairwise comparisons (at a 95% confidence interval) were also performed to compare the control group mean ranking to each of the treatment group mean rankings.

Mean scores for lameness improved for all three treatment groups when compared with the control group. The control group lameness mean score was lowest of the four trial groups on the initial evaluation with a mean of 0.833, and increased to 1.417 at the end of the trial period. The three treatment groups started the trial with mean scores of 1.455 (acidified ionized copper solution), 1.091 (oxytetracycline 100 mg/cc), and 1.0 (acid/chlorite composition of Example 1). At the end of the trial, all three treatment groups had lower mean scores, with 0.364 for the acidified ionized copper solution, 0.455 for the oxytetracycline solution, and 0.20 for the acid/chlorite composition.

When the change in lameness scores for the three treatment groups over the three-week trial period was examined and compared to the change in the control group, all three groups of cows showed significant (p<0.05) improvement in locomotion scores. These results are presented in Table 1 and illustrated in FIG. 1.

TABLE 1

Mean Lameness Scores over the Three Week Trial Period

| Treatment Group | Week 0 | Week 1 | Week 2 | Week 3 | Mean Change |
|---|---|---|---|---|---|
| Copper solution | 1.455 | 0.636 | 1.091 | 0.364 | −1.091 |
| Acid/chlorite | 1.000 | 1.100 | 0.900 | 0.200 | −0.800 |
| Oxytetracycline | 1.091 | 0.545 | 0.727 | 0.455 | −0.636 |
| Control | 0.833 | 1.167 | 1.167 | 1.417 | 0.583 |

These results show that lameness scores improve within a three-week treatment period with topical application of the three compositions tested, with the lowest lameness score observed in cows treated with the acid/chlorite composition of Example 1.

From the foregoing it will be appreciated that, although specific embodiments of the invention have been described herein for the purpose of illustration, various modifications may be made without deviating from the spirit and scope of the invention.

We claim:

1. A method for treating bovine hairy heel warts, comprising applying to a bovine hairy heel wart an effective amount of an aqueous composition comprising a protic acid and a chlorite ion, wherein the protic acid is present in an amount ranging from about 0.005% to about 5% by weight of the composition, and wherein the chlorite ion is present in an amount ranging from about 0.01% to about 1.0% by weight of the composition.

2. The method of claim 1 wherein the protic acid is an organic acid present in an amount ranging from about 0.05% to about 5% by weight of the composition.

3. The method of claim 2 wherein the organic acid is present in an amount ranging from about 0.1% to about 0.5% by weight of the composition.

4. The method of claim 2 wherein the organic acid is mandelic acid.

5. The method of claim 1 wherein the protic acid is an inorganic acid present in an amount ranging from about 0.005% to about 2% by weight of the composition.

6. The method of claim 1 wherein the chlorite ion is provided by a metal chlorite.

7. The method of claim 6 wherein the metal chlorite is sodium chlorite.

8. The method of claim 1 wherein the composition further comprises an agent selected from the group consisting of a wetting agent, a film forming agent, an alcohol, a wound-healing agent, a preservative and a colorant.

9. The method of claim 1 wherein the wound-healing agent is a copper-containing compound.

10. The method of claim 9 wherein copper is present in the composition in an amount ranging from 100 ppm to 4000 ppm.

11. The method of claim 1 wherein the application is by spraying.

12. The method of claim 1, further comprising the step of mixing a first phase and a second phase prior to applying the composition to the bovine hairy heel wart, wherein the first phase comprises the protic acid and the second phase comprises the chlorite ion.

* * * * *